United States Patent [19]

Lange

[11] Patent Number: 5,321,151
[45] Date of Patent: Jun. 14, 1994

[54] PROCESS FOR PREPARATION OF IODOPROPARGYL CARBAMATES

[75] Inventor: Barry C. Lange, Lansdale, Pa.

[73] Assignee: Rohm and Haas Company, Philadelphia, Pa.

[21] Appl. No.: 76,660

[22] Filed: Jun. 14, 1993

[51] Int. Cl.$^5$ ............................................. C07C 261/00
[52] U.S. Cl. ............................................................ 560/167
[58] Field of Search ............................................. 560/167

[56] References Cited

U.S. PATENT DOCUMENTS

| | | | |
|---|---|---|---|
| 4,661,632 | 4/1987 | Oeckl | 564/217 |
| 4,841,088 | 6/1989 | Kusaba | 558/417 |
| 4,945,109 | 3/1990 | Rayuda | 514/478 |
| 5,183,927 | 2/1993 | Utsunomiya | 560/115 |
| 5,194,660 | 3/1993 | Leung | 560/24 |
| 5,209,930 | 5/1993 | Bowers-Daines | 424/401 |
| 5,219,875 | 6/1993 | Sherba et al. | 514/373 |

FOREIGN PATENT DOCUMENTS

| | | |
|---|---|---|
| 14032 | 6/1980 | European Pat. Off. . |
| 513541 | 11/1992 | European Pat. Off. . |
| 539092 | 4/1993 | European Pat. Off. . |
| 10910 | 6/1964 | Japan . |
| 2220000 | 8/1989 | United Kingdom . |

*Primary Examiner*—Paul J. Killos
*Attorney, Agent, or Firm*—Michael B. Fein

[57] ABSTRACT

Process for preparing iodopropargyl carbamate compounds comprising reacting:
  A. an alkyl($C_1$-$C_6$)amine;
  B. liquid, supercritical carbon dioxide;
  C. propargyl alcohol; and
  D. optionally a catalyst;

to form N-alkyl($C_1$-$C_6$) propargyl carbamate; followed by reaction with an iodinating agent is disclosed.

6 Claims, No Drawings

PROCESS FOR PREPARATION OF IODOPROPARGYL CARBAMATES

I. BACKGROUND OF THE INVENTION

A. FIELD OF THE INVENTION

This invention is in the field of chemical processes for preparation of iodopropargyl carbamates.

B. DESCRIPTION OF THE PRIOR ART

Polyphase ® fungicide is one of the leading paint mildewcides in the market place currently. The active ingredient is N-butyl iodopropargyl carbamate.

Troy Chemical Corporation U.S. Pat. No. 3,923,870 discloses what is presumed to be the commercial process for preparing N-butyl iodopropargyl carbamate. ICI European Pat. Appl. 0014032 published Jun. 6, 1990 discloses reacting an alkynol with an isocyanate and followed by iodination. The Troy and ICI disclosed processes use butyl isocyanate which is presumably produced from the reaction of butyl amine with phosgene. Isocyanates are generally toxic and are hazardous materials to handle. Troy's more recent process patent, GB 222 0000 published Jun. 23, 1989, discloses a method which uses as a starting material alkynyl chloroformate which is presumably produced from the reaction from propargyl alcohol and phosgene. Alkynyl chloroformate is also toxic, unstable, and hazardous. Although phosgene is a cheap raw material, it is also a very hazardous material. Presumably the cost of production of N-butyl iodopropargyl carbamate is greatly influenced by the procedures necessary for the safe handling of phosgene.

EP patent publication 0539092 A (U.S. Ser. No. 07/782,039) assigned to Rohm and Haas, the same assignee as the present invention, also discloses a process for the preparation of N-butyl iodopropargyl carbamate that avoids the use of phosgene and isocyanates.

II. SUMMARY OF THE INVENTION

It is an object of the present invention to provide an improved process for preparation of iodopropargyl carbamates. A further object is to provide such a process wherein phosgene or butyl isocyanate need not be handled. Production of N-butyl iodopropargyl carbamate is also an object of a preferred embodiment of the invention. A still further object is to provide a process which does not require the hazardous raw materials used in prior art processes. A still further object is to provide a process which requires reduced amounts of solvent. A still further object is to provide a process where any unreacted porpargyl alcohol can be recycled.

These objects and others which will become apparent from the following disclosure are achieved by the present invention which comprises in one aspect a process for preparing N-alkyliodopropargyl carbamate compounds comprising reacting:

A. an alkyl($C_1$-$C_6$)amine;
B. liquid, supercritical carbon dioxide;
C. propargyl alcohol; and
D. optionally a catalyst;

to form N-alkyl($C_1$-$C_6$) propargyl carbamate; followed by reaction with an iodinating agent.

III. DETAILED DESCRIPTION OF THE INVENTION AND THE PREFERRED EMBODIMENTS

While the process can be used to produce N-alkyl($C_1$-$C_6$) iodopropargyl carbamates, the preferred product is N-butyl iodopropargyl carbamate.

The first step in the process comprises reacting an alkyl($C_1$-$C_6$)amine with gaseous or liquid, supercritical carbon dioxide. Typically, one equivalent of amine is reacted with from about 5 to about 50 molar equivalents of carbon dioxide, with 10 molar equivalents being preferred. The mixture is agitated for up to 12 hours. Following this reaction, up to 99% of the original amount of carbon dioxide can be removed. To the reaction mixture is added from about 1 to about 10 molar equivalents of propargyl alcohol, with 2 molar equivalents being preferred. The mixture is then agitated with heating (up to 150° C.) and pressurized up from about to 10 to about 50 atm, with 100 atm being preferred. The reaction is completed in from about 0.5 to about 8 hours. The preferred reaction time is 4 hours. Once the reaction is complete, excess propargyl alcohol and any unreacted alkyl($C_1$-$C_6$)amine are removed under reduced pressure. The propargyl alcohol and alkyl($C_1$-$C_6$)amine so removed may be recycled. When employed, typical optional dessicants are in the ranges of from about 2 to about 10 grams, with 5 grams being preferred.

The preferred alkyl amine is n-butyl amine.

Suitable optional catalysts are dessicants, such as silica gel, molecular sieves, and the like; acids, such as acetic acid and sulfuric acid; metal catalysts; and the like.

Iodination may be performed by a variety of methods and reagents known in the literature. These methods include using iodine or an iodine releaser. Suitable iodine releasers are iodine/amino compounds, such as iodine/morpholine comples, and N-iodosuccinimide. Iodine and N-iodosuccinimide are preferred reagents.

When iodine or an iodine/amino complex is used, base should also be used and solvent such as methanol, ethanol, and aqueous ethanol should be used. Suitable bases include sodium carbonate, potassium carbonate, sodium hydroxide, and potassium hydroxide. Preferred bases are sodium or potassium hydroxide. When N-iodosuccinimide is used, a catalyst, such as silver nitrate or the like, should be used in the presence of a solvent such as acetone, methyl ethyl ketone, tetrahydrofuran, and the like. The preferable method of iodination is to react iodine with N-alkyl($C_1$-$C_6$) propargyl carbamate in the presence of sodium hydroxide.

The iodination step is carried out at temperatures of about 0° to about 25° C. for about 20 minutes to about 24 hours.

The following examples illustrate a few embodiments of the invention; however, the invention should not be construed as being limited to these few illustrative embodiments.

EXAMPLE

Synthesis of N-Butyl Iodopropargyl Carbamate

A. One equivalent of n-butylamine is added to a pressurized vessel charged with 10 molar equivalents of liquid, supercritical carbon dioxide. The mixture is agitated at −30° C. at a pressure of 7 atmospheres for 12 hours. Following this, the excess carbon dioxide is removed. To the resulting residue, propargyl alcohol (2 molar equivalents) and dry silica gel (5 grams) is added and the reaction mixture agitated, heated to 150° C. and pressurized to 100 atm. The mixture is reacted under these conditions for 4 hours. Once the reaction is complete, excess propargyl alcohol and unreacted n-butylamine are removed under reduced pressure for recycle, yielding an oil. The oil is taken up in ethyl acetate, washed with water, dried over $MgSO_4$, filtered, and cleaned up with column chromatography (silica gel with ethyl acetate as eluant) to yield a colorless oil.

B. Iodine (3.3 g, 0.013 mol) is added in portions to a stirred solution of the N-butyl propargyl carbamate (4.0 g, 0.026 mole), prepared as above, in ethanol (25 ml), water (10 ml) and 50% sodium hydroxide (2.1 g, 0.026 mol) at 0°-5° C. At the end of the iodine addition, the mixture is stirred at the same temperature for another 5 min. A commercial bleach (18.3 g, 5.25%, 0.013 mole) is then added dropwise to the above solution keeping the temperature at 0°-5° C. At the end of the bleach addition, the light yellow solution is stirred at the same temperature for one hour. Extraction with methylene chloride (2×70 ml) and evaporation of the solvent on a rotary evaporator gives a crystalline residue. Crystallization from hexane/toluene gives the N-butyl iodopropargyl carbamate as needles.

While the invention has been described in sufficient detail for those skilled in the art to be able to make and use it, various alternatives, modifications, and improvements should become apparent from the foregoing disclosure without departing from the spirit and scope of the invention.

I claim:

1. Process for preparing iodopropargyl carbamate compounds comprising reacting:
    A. an alkyl($C_1$-$C_6$)amine;
    B. liquid, supercritical carbon dioxide;
    C. propargyl alcohol; and
    D. optionally a catalyst; to form N-alkyl($C_1$-$C_6$) propargyl carbamate; following by reaction with an iodinating agent, wherein one equivalent of amine is reacted with from about 5 to about 50 molar equivalents of carbon dioxide.

2. Process according to claim 1 wherein said alkyl($C_1$-$C_6$)amine is selected from the group consisting of methyl amine, ethyl amine, propyl amine, and n-butyl amine.

3. Process according to claim 2 wherein one equivalent of amine is reacted with from about 10 molar equivalents of carbon dioxide.

4. Process according to claim 1 wherein said catalyst is selected from the group consisting of dessicants, molecular sieves, acids, metal catalysts.

5. Process according to claim 4 wherein said catalyst is selected from the group consisting of acetic acid and sulfuric acid.

6. Process according to claim 1 wherein said iodinating agent is a mixture of iodine and a base.

* * * * *